United States Patent [19]

Henley et al.

[11] Patent Number: 5,409,542
[45] Date of Patent: * Apr. 25, 1995

[54] AMYLASE RESISTANT STARCH PRODUCT FORM DEBRANCHED HIGH AMYLOSE STARCH

[75] Inventors: Matthew Henley, Somerset; Chung-Wai Chiu, Westfield, both of N.J.

[73] Assignee: National Starch and Chemical Investment Holding Corporation, Wilmington, Del.

[*] Notice: The portion of the term of this patent subsequent to Jan. 25, 2011 has been disclaimed.

[21] Appl. No.: 997,794

[22] Filed: Dec. 29, 1992

Related U.S. Application Data

[63] Continuation-in-part of Ser. No. 857,530, Mar. 25, 1992, Pat. No. 5,281,276.

[51] Int. Cl.$^6$ .......................... C08B 30/00; A23L 1/05
[52] U.S. Cl. .......................... 127/65; 127/32; 127/67; 127/69; 127/71; 426/661
[58] Field of Search .......................... 127/65, 67, 69, 71, 127/32; 426/661

[56] References Cited

U.S. PATENT DOCUMENTS

| | | | |
|---|---|---|---|
| 3,407,070 | 10/1968 | Murray et al. | 426/661 |
| 3,556,942 | 1/1971 | Hathaway | 127/65 |
| 3,728,140 | 4/1973 | Yoshida | 106/210 |
| 3,729,380 | 4/1973 | Sugimoto et al. | 195/31 |
| 3,734,760 | 5/1973 | Hijiya et al. | 106/210 |
| 3,879,212 | 4/1975 | Yoshida et al. | 106/213 |
| 4,428,972 | 1/1984 | Wurzburg et al. | 426/578 |

(List continued on next page.)

FOREIGN PATENT DOCUMENTS

| | | | |
|---|---|---|---|
| 8600936 | 4/1986 | Netherlands. | |
| 1313421 | 4/1970 | United Kingdom | C13L 1/08 |
| WO90/15147 | 12/1990 | WIPO. | |
| WO93/03629 | 3/1993 | WIPO. | |

OTHER PUBLICATIONS

D. Sievert, et al., *Influence of Process Engineering on the Dietary Fiber Fractions of Cereal Foods*, vol. 13 (1989) No. 2, pp. 75–81 month not available.
D. Sievert, et al., *Changes Caused by the Process Engineering of Cereal Technology in Dietary Fibers* vol. 41 (1987) No. 6, pp. 172–177 month not available.
Nutrition and Food Science, *Putting a Figure on Dietary Fibre*, No. 7, pp. 8–10 month not available.
J. A. Cura, et al., *Starch/Starke* 42 (1990) Nr. 5, pp. 171–175 month not available.
C. R. Krisman, et al., *Starch/Starke* 43 Nr. 8, pp. 291–294 month not available.
J. B. South, et al., *Journal of Cereal Science*, (1991) 14, pp. 267–278 month not available.
W. R. Morrion, et al., Chapter 9 in *Methods in Plant Biochemistry*, vol. 2, Academic Press Ltd. (1990) pp. 323–329.
T. Baba, et al., *J. Jpn. Soc. Starch Sci.*, vol. 34, No. 3, pp. 196–202 (1987).
T. Baba, et al., *J. Jpn. Soc. Starch Sci.*, vol. 34, No. 3, pp. 213–217.
C. Mercier, *Die Starke*, 25 Jahrg, 1973 Nr. 3, pp. 78–82 month not available.
C. W. Moore and R. G. Creech, in *Genetics*, 70:611–619, (1972) month not available.
*Corn and Corn Improvement*, Third Edition, 1988, G. F.

(List continued on next page.)

Primary Examiner—Paul Lieberman
Assistant Examiner—Patricia L. Hailey
Attorney, Agent, or Firm—Jane E. Gennaro

[57] ABSTRACT

This resistant starch product is characterized by a specific melting endotherm over a temperature range of 95°–140° C. with a peak in the range of about 115°–135° C. The product is obtained by gelatinizing and then debranching amylose or a high amylose starch with pullulanase or isoamylase.

11 Claims, No Drawings

U.S. PATENT DOCUMENTS

| | | | |
|---|---|---|---|
| 4,780,149 | 10/1988 | Kaper et al. | 127/38 |
| 4,798,735 | 1/1989 | Friedman et al. | 426/578 |
| 4,971,723 | 11/1990 | Chiu | 252/315.3 |
| 5,004,864 | 4/1991 | Robertson et al. | 800/235 |
| 5,009,911 | 4/1991 | Mauro et al. | 426/578 |

(List continued on next page.)

OTHER PUBLICATIONS

Sprague and J. W. Dudley, Editors, American Society of Agronomy, Madison, Wisconsin, pp. 85–115, 124–125 and 399–407 month not available.

Overheads shown at an International Business Communications Conference on Soluble and Insoluble Bulking Agents held in Atlanta, Georgia, Mar. 13, 14, 1991, during presentation entitled "Crystalean–Insoluble Bulking Agent Experimental Approach Toward New Ingredient Development".

Banks, W. and C. T. Greenwood: *Carbohydrate Res.* 6 (1968), 241 month not available.

Greenwood, C. T. and D. J. Hourston: *Starke* 23 (1971), 344 month not available.

Greenwood, C. T., and J. Thomson: *Chem. Ind.,* (1960), 1110 month not available.

Greenwood, C. T. and J. Thomson: *Biochem, J.,* 82 (1962), 156 month not available.

G. K. Adkins and C. T. Greenwood, *Starke,* 18 (1966) 171 month not available.

Greenwood, C. T., and S. MacKenzie: *Carbohydrate Res.,* 3 (1966), 7 month not available.

Adkins, G. K., and C. T. Greenwood: *Starke* 18 (1966), 237 month not available.

Adkins, G. K., and C. T. Greenwood: *Starke* 18 (1966), 240 month not available.

Adkins, G. K., and C. T. Greenwood: *Carbohydrate Res.,* 3 (1966), 81 month not available.

Adkins, G. K., and C. T. Greenwood: *Carbohydrate Res.,* 3 (1966), 152 month not available.

Banks, W., and C. T. Greenwood: *Carbohydrate Res.,* 11 (1969), 217 month not available.

Adkins, G. K., C. T. Greenwood and D. J. Hourston: *Cereal Chem.,* 47 (1970), 13 month not available.

Banks, W., C. T. Greenwood and D. D. Muir: *Starke* 23 (1971), 199 month not available.

Banks, W., C. T. Greenwood and D. D. Muir: *Starke* 26 (1974), 289 month not available.

Journal of Cereal Science 4 (1986) pp. 301–314 *Resistant Starch: Formation and Measurement of Starch that Survives Exhaustive Digestion and Amylolytic Enzymes During the Determination of Dietary Fibre* month not available.

Journal of Cereal Science 6 (1987) pp. 159–172 *Formation of Enzyme Resistant Starch During Autoclaving of Wheat Starch: Studies* in vitro and in vivo month not available.

Asp, et al., *Enzyme Resistant Starch Fractions and Dietary Fibre,* pp. 29–32 month not available.

Cereal Foods World, vol. 34, No. 5 (May 1989) pp. 415–421 *Microstructural, Physiochemical, and Macromolecular Changes in Extrusion–Cooked and Retrograded Corn Starch.*

Journal of Applied Polymer Science, vol. 11 (1967) pp. 481–498 *Colloidal Macromolecular Phenomena Part I. Novel Microcrystals of Polymers* month not available.

Journal of Cereal Science 8 (1986) pp. 203–106 *Physical Chemical Characterization of Resistant Starch from Wheat* month not available.

Journal of Cereal Science 9 (1989) pp. 1–15 *Characterization of Resistant Starch from Wheat and Maize* month not available.

Journal of Cereal Science 4 (1986) pp. 315–323 *Effects of Various Thermal Processes on Dietary Fibre and Starch Content of Whole Grain Wheat and White Flour* month not available.

Cereal Chemistry, vol. 61, 1984, *Extrusion Cooking and Dietary Fiber: Effects on Dietary Fiber Content and on Degradation in the Rat Intestinal Tract* month not available.

*Characterization of Resistant Starch from Autoclaved*

(List continued on next page.)

U.S. PATENT DOCUMENTS

| | | | |
|---|---|---|---|
| 5,035,912 | 7/1991 | Furcsik et al. | 426/578 |
| 5,051,271 | 9/1991 | Iyengar et al. | 426/658 |
| 5,169,662 | 12/1992 | Spicer | 426/449 |
| 5,176,936 | 1/1993 | Creighton et al. | 426/618 |

OTHER PUBLICATIONS

*Wheat Starch,* Starch/Starke 41 (1989), pp. 147–151 month not available.

Englyst, et al., *Resistant Starch, Its Physical Role in Man and Its Measurement in Foods,* pp. 37–38 month not available.

Apr. 1987 Faseb Abstract Form.

Ca. Inst. Food Sci. Technol. J. vol. 17, No. 2 pp. 65–70, 1984 *Textural and Microstructural Changes in Corn Starch as a Function of Extrusion Variables,* J. Owusu-Ansah, et al. month not available.

Cereal Chemistry, vol. 52, May–Jun. 1975, No. 3, part I, pp. 283–297 *Modification of Carbohydrate Components by Extrusion-Cooking of Cereal Products,* C. Mercier, et al.

Cereal Chem. 65(2):138–143, *Relationship Between Amylose Content and Extrusion-Expansion Properties of Corn Starches,* R. Chinnaswamy, et al. month not available.

Cereal Sci. Today, Sep. 1973, vol. 18, No. 9, p. 286, *Changes in Various Starches by Cooking-Extrusion Processing: II Physical Structure of Extruded Products.*

Journal of Food Science, *vol. 58, No. 6, 1992, Raw-Starch Degrading Amylase(s) Affect Enzyme-Resistant Starch,* pp. 1443–1444, L. Gruchala, et al. month not available.

Journal of Food Science, vol. 48, (1983), *Changes in Starch Fraction During Extrusion-Cooking of Corn,* M. H. Gomez, et al. month not available.

Cereal Chemistry, vol. 61, No. 6, 1984, *Extrusion Cooking and Drum Drying of Wheat Starch. I. Physical and Macromolecular Modifications,* P. Colonna, et al. month not available.

Lecture presented at the 27th Starch Convention of the Arbeitsgemeinschaft Getreideforschung in Germany from Apr. 28 to 30, 1976, *Effect of Extrusion-Cooking on Potato Starch Using a Twin Screw French Extruder,* C. Mercier.

Cereal Chemistry, vol. 70, No. 2, Mar.–Apr. 1993, *Enzyme-Resistant Starch: Studies Using Differential Scanning Calorimetry,* L. Gruchala and Y. Pomeranz.

AMYLASE RESISTANT STARCH PRODUCT FORM DEBRANCHED HIGH AMYLOSE STARCH

This is a continuation-in-part of U.S. patent application Ser. No. 07/857,530, filed Mar. 25, 1992, now U.S. Pat. No. 5,2821,276.

BACKGROUND OF THE INVENTION

It is known that the amylose fraction of starch retrogrades to form a starch resistant to alpha-amylase digestion, and that this resistant starch is beneficial as a dietary component contributing to the total dietary fiber content in food products. See, for example, C. S. Berry, "Putting a figure on dietary fibre," *Nutrition and Food Science* 93 (1985) 8–10; C. S. Berry, "Resistant Starch: Formation and Measurement of Starch that Survives Exhaustive Digestion with Amylolytic Enzymes during the Determination of Dietary Fibre," *Journal of Cereal Science* 4 (1986) 301–314; and N-G. Asp, et al., "Formation of Enzyme Resistant Starch During Autoclaving of Wheat Starch: Studies in vitro and in vivo," *Journal of Cereal Science* 6 (1987) 159–172.

U.S. Pat. Nos. 3,729,380 and 3,324,760 disclose a method for preparing a low molecular amylose by gelatinizing starch, cooling it, and selectively hydrolyzing the branched parts in amylopectin with alpha-1,6-glucosidase. U.S. Pat. 5,051,271, and PCT application WO 90/15147 of Pomeranz et al. call for a cycle, or repeated cycles, of heating and cooling to form an alpha-amylase resistant starch that can be further purified by enzyme or chemical hydrolysis.

The starch material obtained by these methods is reported by Sievert and Pomeranz, *Cereal Chemistry* 67 (1990) 21, to exhibit a melting transition over two zones: one at 80°–107° C. with a 95° C.; the other at 120°–166° C. with a peak at 153° C. The peak at 95° C. disappear sample was defatted indicating this peak corresponded to the lipid complexation of amylose. The peak at 153° C. corresponded to a melting endotherm exhibited by the amylase resistant fraction (i.e. retrograded amylose). These data are consistent with those shown by Ring, et al. in *Carbohydrate Research* 162, (1989) 277, describing the melting of an amylopectin gel at 59° C. and of an amylose gel at 153° C.

SUMMARY OF THE INVENTION

This invention is a thermostable, partially crystalline, debranched starch product resistant to alpha-amylase digestion and characterized by a melting endotherm distinct from melting endotherms reported in the prior art. It has crystalline regions characterized by a melting endotherm with a peak in the range of about 115°–135° C., and amorphous regions characterized by a solubility in water at room temperature of greater than 7%. The starch product has a molecular weight in the range of 15,000–100,000 for the majority (greater than 80%) of the starch molecules. The starch is made by a process consisting of: (a) preparing an aqueous slurry of a starch that contains at least 40% amylose; (b) gelatinizing the starch slurry by high shear, high temperature cooking; (c) adding an effective amount of a debranching enzyme to the gelatinized starch to hydrolyze the 1,6-glucosidic bonds of the starch molecules; and (d) isolating the resistant starch product by extrusion or spray drying. In another embodiment, the starch product is isolated by adding an effective amount of an inorganic salt to the debranched starch and incubating the starch and salt mixture at temperatures between 50°–100° C. to cause precipitation of the starch product. This starch product when added to foods will contribute to the total dietary fiber present in the foods.

DETAILED DESCRIPTION OF THE INVENTION

The starches used in preparing the resistant starch of this invention may be derived from any source containing amylose, for example, from corn, potato, barley, sweet potato, wheat, rice, sago, tapioca, and sorghum, and may be defatted or chemically modified. However, the preferred starting starch contains greater than 40% amylose, for example, HYLON V, a corn starch containing about 50% amylose, or HYLON VII, a corn starch containing about 70% amylose, both products of National Starch and Chemical Company, Bridgewater, N.J.

The starting starch is dispersed into an aqueous slurry having a solids content of 5%–40%, preferably about 15%–20%, and heated at sufficient temperature and pressure to effect gelatinization. Although gelatinization may be effected by any of the methods known in the art, the preferred method is to use high temperature and high shear by forcing the starch slurry through a jet cooker. Jet-cookers are well known in the industry and consist of a cooking chamber in which the starch slurry is contacted with live steam under elevated temperatures. Generally, the conditions for gelatinization are temperatures from 120°–175° C. (250°–350° F.), and pressures from 1.05–10.5 kg/cm$^2$ (15–150 psi). Complete gelatinization is determined visually as total disintegration of granular structure. The gelatinization process disrupts, in whole or in part, the associative bonding of the starch molecules within the raw starch granule, preparing the starch molecules for debranching.

After the starch has been gelatinized, the starch solids content is adjusted to the highest feasible solids level (to keep the amount of water as low as possible to facilitate subsequent drying of the starch), the preferred solids content being about 15%–20%. A higher solids starch system may be employed if the starch is processed with adequate mixing to uniformly blend enzyme and starch at the higher solids.

After the solids content is fixed, the temperature and pH of the starch dispersion are readjusted to provide optimum enzyme activity. These parameters will vary depending upon the type and source of enzyme used, the enzyme concentration, the substrate concentration, and the presence or absence of inhibitors.

The preferred enzyme for the enzymatic debran of this process is pullulanase (E. C. 3.2.1.41; pullulan 6-glucanohydrolase), a heat stable enzyme obtained from a species of Bacillus. Pullulanase will catalyze the hydrolysis of the alpha-1,6 linkages in pullulan and starch, provided that there are at least two glucose units in the side chain. However, other endo-alpha-1,6-glucanohydrolases, such as isoamylase (E.C. 3.2. 1.68), or any other endo-enzyme that exhibits selectivity in cleaving the 1,6-linkages of the starch molecule, leaving the 1,4-linkages substantially intact, may be used to debranch starch according to this method.

When the enzyme used is the Bacillus pullulanase, and the starch solids content is in the range of 5%–40%, the reaction may be carried out in a pH range from 3.0–7.5, preferably from 4.5–5.5, and most preferably at 5.0. Buffers, such as acetates, phosphates, citrates, or the salts of other weak acids can be added to ensure that the pH will be at the optimum level throughout the debranching. At pH 5.0 the preferred temperature for the aqueous starch dispersion during the enzymatic debranching by the Bacillus pullulanase will be between 25°–75° C., the more preferred being between 50°–65° C., and the most preferred being 60° C. If shorter treatment times are desired, the optimum temperature range can be increased to 60°–65° C. (or higher, if the debranching enzyme is thermally stable at the higher temperatures), or a higher enzyme concentration can be used. As with other parameters of the enzyme reaction, the preferred and optimum temperature ranges will vary with changes in other parameters that affect enzyme activity, such as substrate concentration and pH, and these can be determined by the practitioner.

Optimum concentrations of enzyme and substrate are governed by the level of enzyme activity, which will vary depending upon the enzyme source, the enzyme supplier, and the concentration of the enzyme provided in commercially available batches. In general, the pullulanase enzyme is effective at 1500 PUN (pullulanase units novo)/kg starch using a HYLON V or VII starch substrate at 15% solids content. Although the process of this invention makes use of an enzyme in solution, an enzyme immobilized on a solid support is intended to fall within the scope of this invention.

The enzymatic treatment is permitted to continue until essentially complete debranching has occurred, which in most systems under optimum enzymatic conditions will be in less than 24 hours. The enzyme is then deactivated by increasing the temperature of the starch dispersion to at least 75° C. for about 15 minutes, or alternatively, by adjusting the pH of the starch dispersion to below 3.0 and holding at that pH for about ½ hour.

After debranching and deactivation of the enzyme, the starch is isolated by extrusion or spray drying, flash drying, air drying, freeze drying, vacuum drying, belt drying, drum drying, or any other method known and used in the art for drying starch. However, the extrusion process has been found to increase the yield of resistant starch and it is the preferred method. The extrusion apparatus can be any screw-type extruder, although the twin-screw extruder is preferred. A twin-screw extruder will typically have rotating screws in a horizontal cylindrical barrel with an entry port mounted over one end and a shaping die mounted at the discharge end. When twin screws are used, they may be co-rotating and intermeshing or non-intermeshing. Each screw will comprise a helical flight or threaded section and typically will have a relatively deep feed section followed by a tapered transition section and a comparatively shallow constant-depth meter section. The screws, which are motor driven, generally fit snuggly into the cylinder or barrel to allow mixing, heating and shearing of the material as it passes through the extruder.

Heat is provided through a channel, chamber or bore located in the barrel wall which contains an electrical calrod or coil, or a circulating heated medium, such as oil. The heat exchange means may also be placed in or along the shaft of the screw device. The starch is extruded at temperatures between 60°–180° C., preferably between 110°–180° C. and temperature is controlled in zones along the length of the screw Variations in any of the elements used in the extruder may be made as desired in accordance with conventional design practices in the field.

In another embodiment, the resistant starch product is isolated by adding an inorganic salt to the starch dispersion and incubating the mixture at 50°–100° C., preferably 90°–100° C. The salt known salt that will not interfere with starch retrogradation and that will act to precipitate the resistant starch. Suitable salts are sodium sulfate, ammonium sulfate or magnesium sulfate, and sodium chloride, preferably are the sulfate salts, and are added to the deactivated starch slurry in a minimum of 10% of the solids content, preferably from 25%–50%.

The resistant starch product prepared by this method shows a melting endotherm for the resistant fraction within the range of 115°–135° C., more typically within the range of 119°–123° C. and greater than 7% in water.

The following examples disclose procedures for the production of the starch products of this invention and an analytical comparison of those starches with starches produced by prior art methods. The samples were analyzed for dietary fiber by the Prosky method as outlined in Example 9.

EXAMPLE

Reference Example 1

This sample uses a waxy maize containing no amylose as the starting starch. Waxy corn starch (0% amylose) (1000 g) was slurried into water and jet cooked at temperatures between 149°–160° C. (300°–320° F.). The starch was placed into a constant temperature bath set at 60° C. and benzoate (approximately 0.1% by weight of the starch) was added to the cooked starch to preserve freshness. The starch dispersion was diluted to a solids range of about 15%. The pH was adjusted to 5.0 with a solution of 3:1 water/concentrated HCl. Promozyme 200L (75 ml), a commercial preparation of pullulanase, a product of NOVO-NORDISK, Danbury Conn., was added when the starch temperature reached 60° C. (140° F.). The enzyme was allowed to debranch the starch for 48 hours and then was deactivated by lowering the pH to 2.7–3.0 with a solution of 3:1 water/concentrated HCl for ½ hour. The starch was neutralized to a pH of 5.0–5.5 with 3% NaOH in water. The product was collected as a dry powder in 100% yield by spray drying using an Anhydro portable spray dryer (Lab type, S1, Anhydro Corp., Copenhagen, Denmark) having an inlet temperature of 210°–215° C., and outlet temperature of 90°–100° C. A atomizing nozzle with air pressure at 2.10 kg/cm$^2$ (30 psi) was used to atomize the starch. The powder was found to contain 1.0% dietary fiber when assayed by the Prosky method.

Inventive Example 2

This example shows the preparation of resistant starch using 100% amylose and HYLON VII containing 70% amylose as the starting starches, and varying methods of drying and recovering.

A. This sample uses 100% amylose as the starting starch. Potato starch (100 parts, d.b.) and sodium sulfite (1 part) were added to 1300 parts of a 10% solution of magnesium sulfate (130 parts anhydrous magnesium sulfate in 1170 parts water). The pH was adjusted to 7.5 with 25% H$_2$SO$_4$. The slurry was then passed through a thermal converter with a pump pressure of 7.03 kg/cm$^2$ (100 psi), pump speed of 7.56 liters per min (2 gal/min), temperature of 158° C. (315° F.), with 1 minute dwell time highest possible steam input (>90%). After cooking, the percent solids were determined to be 14% (corresponding to 8.0% MgSO$_4$ and 6.0% potato starch). (At this point, the salt concentration should be within 8.0%–9.5%, and if not in this range can be brought to this concentration by either dilution with water or addition of $MgSO_4$.) The solution was cooled to 20° C. and allowed to age for 20 hours while being slowly agitated. After aging, the amylose was recovered by centrifuging and washed by repeated suspension in water followed by centrifuging. The product was air dried and dispersed at 15% solids in water. The slurry was jet cooked at about 155° C. (310° C.). It was debranched with 18.75 ml Promozyme following the method of Example 1A. The reaction was allowed to proceed for 24 hours, after which the enzyme was deactivated with acid. The sample was recovered by spray drying according to the method of Example 1A. This sample was found to contain 50.3% dietary fiber when analyzed by the Prosky method.

B. Spray dried. HYLON VII starch (2 kg) was slurried into water (11.31 kg) and jet cooked at 149°–158° C. (300°–315° F.). The starch was placed into a constant temperature bath set at 60° C. and benzoate (2 g) was added to the cooked starch to preserve freshness. The dispersed starch was adjusted to pH 5.0 with a solution of 3:1 water/concentrated HCl. Promozyme 200L (140 ml) was added when the starch temperature reached 60° C. (140° F). The enzyme was allowed to debranch the starch for 48 hours and then was deactivated by lowering the pH to 2.7–3.0 with a solution of 3:1 water/concentrated HCl for ½ hour. The starch was neutralized to a pH of 5.0–5.5 with 3% NaOH in water. The sample was divided into two parts. One part was spray dried according to the method of example 1A. This sample was found to contain 25% dietary fiber when analyzed by the Prosky method.

C. Extruded. The remaining part of Example 2-A was extruded on a Warner & Pfleiderer Type ZSK-30 twin-screw extruder. The screw configuration used is designated 12–44 and was used with a 5 mm (×2) die. The screws were operated at a speed of 400–450 rpm and the barrel heating zones were set to 60°/100°/120°/150°/150° C. The barrel was placed under a vacuum of 35–40 cm Hg (14–16 inches Hg) through a single barrel vent. The extruded starch rope was air dried and ground to a fine powder. This sample was found to contain 30.0% dietary fiber when analyzed by the Prosky method.

D. Defatted starch, Spray dried. Granular HYLON VII was defatted by repeated extraction with methanol using a Soxleht extractor for ten days. A portion of this defatted starch (500 g) was then debranched and spray dried according to the method of Example 1. This sample was found to contain 32.4% dietary fiber when analyzed by the Prosky method.

F. Salt precipitation. A debranched HYLON VII suspension was prepared according to the method of Example 1 and $MgSO_4$ was added in an amount equivalent to 25% by weight of the solids of the suspension. The salt and starch suspension was heated to 95° C. and held at that temperature for 24 hours. The sample was cooled to about 25° C. and ethanol was added to bring the solvent to a solution of 50:50 ethanol:water and to precipitate out the starch product. The product was filtered over a Buchner funnel, washed twice with 50:50 ethanol:water and air dried. The sample was found to contain 40.9% dietary fiber when analyzed by the Prosky method.

Comparative Example 3

This example shows the production of resistant starch using processes known in the art.

A. Method of PCT application WO 90/15147 of Pomeranz et al. HYLON VII starch (2 kg) was slurried into water (8.65 kg) and poured into #1 retort canning jars. The starch was retorted at 126°–127° C. (260° F.) for two hours, and cooled in the retort to 25° C. The starch was then cooled at 4° C. for 72 hours. The starch was brought to room temperature, removed from the retort cans, broken to a smaller size and slurried in deionized water to a concentration of about 10% starch solids. This slurry was further comminuted using an Eppenbach homogenizer on high speed. The pH of the slurry was adjusted to 6.3 with 3% NaOH in water and the slurry heated to 90°–95° C. in a boiling water bath. Termanyl 120L (alpha-amylase, a product of NOVO) was added (5 ml per 100 grams starch) and the enzyme and starch slurry incubated for 60 minutes at that temperature. The enzyme was deactivated by lowering the pH to 3.0 with a solution of 3:1 water/concentrated HCl for ½ hour. The starch was neutralized to a pH of 5.0–5.5 with 3% NaOH in water. The mixture was centrifuged and the insoluble components isolated by removing the soluble components by decanting the supernatant; this step was repeated after resuspending the insolubles in deionized water. The insolubles were further isolated by resuspension in deionized water followed by filtration over Whatman 54 paper in a Buchner funnel. The insoluble product was air dried and ground to a fine powder. This sample was found to contain 47% dietary fiber when analyzed by the Prosky method.

B. Method of U.S. Pat. No. 5,051,271 issued to Iyengar et al. High amylose starch (150 g) was suspended in 400 ml of water to make a smooth, homogeneous slurry. This slurry was added to 2.6 L of boiling (autoclaved) water with constant stirring. The resulting suspension was autoclaved at 121° C. for 8 hours. The solution was cooked and incubated at 24° C. for 16 hours and then at 8° C. for 120 hours. Resistant amylose that precipitated during this process was removed from the suspension by repeated centrifugation and resuspended at 10% solids with stirring to form a smooth, homogeneous suspension. The 10% starch solids suspension was then subjected to enzymatic hydrolysis. Two enzyme suspensions were prepared separately: 1.4 g of HT (HT-proteolytic, Solvay Enzymes, Elkhart, IN) concentrated alpha-amylase were added to 26.6 ml of water, and 2,500 U human salivary amylase (Sigma Type 1X-A) were added to 100 ml deionized water. Both of the amylase solutions were then added to the starch suspension and the reaction mixture stirred at 23° C. for 24 hours. The resulting enzyme-modified resistant starch (EMRS) was removed from the suspension by repeated centrifugation. The solid was dispersed in water to form a 10% (w/w) suspension and freeze-dried. This sample was found to contain 52% dietary fiber when analyzed by the Prosky method.

C. Method of U.S. Pat. 3,734,760 assigned to Hayashibara A 15% amylomaize starch suspension (1 liter) (amylose content 70%) was gelatinized by heating with agitation at 165° C. for 10 minutes in a pressure cooker (Buechiglasuster, Fabik-Nr 106703, 1644 HBZ). The cooked starch was cooled rapidly to 60° C. Thereafter, purified isoamylase (EC 3.2.1.68) enzyme derived from Pseudomonas (Sigma Chemical, cat.#1.2758), 125,000 units, was added to the gelatinized solution and incubated at 45° C. for two days in a reciprocating incubator. The amylose mixture was cooled to -5° C. and precipitated out. The starch was recovered by freeze-drying (Dura-Top MP, FTS Systems, Stone Ridge, N.Y.). This sample was found to contain 12.2% dietary fiber when analyzed by the Prosky method.

Example 4

DSC procedure. This example shows the procedure used for obtaining differential scanning calorimetry data. DSC measurements were performed on each of the samples with a Perkin-Elmer DSC-4 instrument equipped with a 3600 thermal analysis data station and a Perkin-Elmer graphics plotter 2 (Perkin-Elmer Corporation, Instrument Division, Norwalk, Conn.). Samples of -12 mg were weighed accurately into Perkin-Elmer stainless steel pans. About 40 μl of deionized water were added and the pans were sealed and allowed to equilibrate overnight to 4° C. The DSC scan was run from 50°–180° C at 10° C./min heating rate. An empty pan represented the reference sample. The peak transition temperature ($T_p$) was defined and read as the temperature at the peak maximum.

Example 5

Solubility procedure. This example shows the procedure used for obtaining solubilities of the samples. Solubility was determined by measuring the difference in the optical rotation of a 0.5% starch dispersion and of the supernatant of the dispersion after centrifugation on a Perkin-Elmer #141 Polarimeter equipped with a sodium lamp.

The starch was first blended in a Waring blender equipped with a semi-micro stainless steel cup. Approximately 30–40 ml of distilled water were added into the blender cup. With the blender on low speed, approximately 0.50 gram of starch (as is) was dispersed into the water within 15–30 seconds. The speed was increased to high and the starch agitated for 2 minutes. The solution was transferred to a 50 ml volumetric flask and diluted to mark with distilled water. This was designated the stock solution. The stock solution was shaken well and divided into two portions by removing 25 ml by pipet. The stock solution remaining was reshaken, dispersed with 10 ml of 5N KOH, and diluted to the 50 ml mark with distilled water. The 25 ml sample removed by pipet was transferred to a 50 ml centrifuge tube, and spun down in an International Model K centrifuge at 1800–2000 rpm for 15 minutes. Then 12.5 ml of supernatant was transferred by pipet to a 25 ml volumetric flask, 5 ml of 5N KOH was added with swirling, and the supernatant diluted to the 25 ml mark with distilled water. The optical rotation of both the stock solution and the supernatant sample solution were measured in a 0.998 cm polarimeter cell and the percent water solubles determined by the following equation.

$$\% \text{ Water Solubles} = \frac{\text{Optical Rotation of Supernatant } (\alpha)/\text{Path Length of Supernatant}}{\text{Optical Rotation of Stock Solution } (\alpha)/\text{Path Length of Stock Solution}} \times 100$$

Example 6

Digestibility Determination. This example shows the procedure used for determining the digestibility of the samples by alpha-amylase. The digestibility was determined by measuring the difference in the concentration of a 0.5% starch dispersion and of the supernatant of the dispersion after digestion with alpha-amylase and centrifugation. The optical rotation was measured on a Perkin-Elmer #241 Polarimeter equipped with a 1.002 cm cell, a continuous sodium lamp, a continuous Na/589 filter/source, having a recorder range of ±/5 degrees and an integration speed of 0.1 seconds. A 0.5 ml aliquot of Sigma-A6255 Lot 60H8045 porcine pancreas alpha-amylase (16,800 units) was dissolved into 14.5 ml of 0.5M phosphate buffer at pH 7.5. A one gram sample of starch and 5 ml of enzyme solution were dispersed into a 50 ml volumetric flask, diluted to mark with the buffer solution. The dispersion was transferred to a 50 ml Erlenmeyer flask, the flask was placed in a shaker/incubator at 37° C. for two hours. A 2.5 ml sample was removed, diluted to 0.5% solids with buffer solution, and centrifuged at 2000 rpm for 10 minutes. A specimen of the supernatant was removed and the optical rotation measured. The percent digestibility determined by the following equation in which 203 is the constant for the rotation of starch in water.

$$\% \text{ Digestibility} = \frac{\text{Optical Rotation of Supernatant } (\alpha)/\text{Path Length of Supernatant} \times 203}{0.005} \times 100$$

Example 7

Molecular Weight Determination. This example shows the procedure used for determining molecular weight by gel permeation chromatography. Samples were prepared for analysis by slurrying 5 mg starch in 4 ml of dimethylsulfoxide (DMSO) containing 0.03M sodium nitrate and heating the slurry to 80° C. for at least 30 minutes. Samples in the amount of 200 microliters were injected into an ALC/GPC-150° C. Chromatograph (Waters Associates, Milfor, Mass.) equipped with a Nelson 3000 Series Chromatography Data System and two PL gel mixed 10 micromol columns (obtained from Polymer Laboratory, Amherst, Mass.) employing DMSO containing 0.03M sodium nitrate as the mobile phase, and eluted at a rate of 1 ml/min. The column was calibrated using dextran standards with molecular weights of 2,000, 20,000, 80,000, and 500,000 (obtained from Pharmacia Fine chemicals, Piscataway, N.J.). The molecular weight is recorded as the peak molecular weight integrated by the data system.

Example 8

Total Dietary Fiber Determination. This example outlines the Prosky Method for determining dietary fiber in foods according to Prosky, et al., J. Assoc. Off. Anal. Chem., 68, 677 (1985). Reagents:
  (a) Ethanol 95% v/v, technical grade.
  (b) Ethanol 78%. Place 207 ml H$_2$O into 1 L volume flask. Dilute to volume with 95% EtOH. Mix and dilute to volume again with 95% EtOH if necessary. Mix.
  (c) Acetone, reagent grade.
  (d) Phosphate buffer, 0.05M, pH 6.0. Dissolve 0.875 g Na phosphate dibasic, anhydride (Na$_2$HPO$_4$) (or 1.097 g dihydrate) and 6.05 g Na phosphate monobasic monohydrate (NaH$_2$PO$_4$) (or 6.8 g dihydrate) in ca 700 ml H$_2$O. Dilute to 1 L with H$_2$O. Check pH with pH meter.

(e) Termamyl (heat stable α-amylase) solution - No. 120 L, Novo Laboratories, Inc., Wilton Conn. 06897. Keep refrigerated.

(f) Protease. No. P-5380, Sigma Chemical Company. Keep refrigerated.

(g) Amyloglucosidase. No. A-9268, Sigma Chemical Company. Keep refrigerated. Alternatively, a kit containing all 3 enzymes (pretested) is available from Sigma Chemical Company, Catalog No. KR-185.

(h) Sodium hydroxide solution, 0.171N. Dissolve 6.84 g NaOH ACS in ca 700 ml $H_2O$ in 1 L. volume flask. Dilute to volume with $H_2O$.

(i) Phosphoric acid solution, 0.205M. Dissolve 23.64 g $H_3PO_4$ ACS (85%) in $H_2O$ in 1 L volume flask. Dilute to volume with $H_2O$.

(j) Celite C-211, acid-washed. Fisher Scientific Company.

Method: Run blank through entire procedure along with samples to measure any contribution from reagents to residue.

Homogenize sample and dry overnight in 70° C. vacuum oven, cool in desiccator, and dry-mill portion of sample to 0.3-0.5 mm mesh.

Weigh duplicate 1 g samples, accurate to 0.1 mg, into 400 ml, tall-form beakers. Sample weights should not differ by >20 mg. Add 50 ml pH 6.0 phosphate buffer to each beaker. Check pH and adjust if necessary. Add 0.1 ml Termanyl solution. Cover beaker with Aluminum foil and place in boiling $H_2O$ bath 15 minutes. Shake gently at 5 minute intervals. Increase incubation time when number of beakers in boiling $H_2O$ bath makes it difficult for beaker contents to reach internal temperature of 100° C. Use thermometer to ascertain that 100° is attained at 15 minutes. Total of 30 minutes in $H_2O$ bath should be sufficient.

Cool solutions to room temperature. Adjust to pH 7.5±0.1 by adding 10 ml 0.171N NaOH solution.

Add 5 mg protease. (Protease sticks to spatula, so it may be preferable to prepare enzyme solution just before use with ca 0.1 ml phosphate buffer and pipet required amount).

Cover beaker with aluminum foil. Incubate 30 minutes at 60° C. with continuous agitation. Cool. Add 10 ml 0.205M $H_3PO_4$ solution to adjust pH to 4.5±0.2. Add 0.3 ml amyloglucosidase, cover aluminum foil and incubate 30 minutes at 60° C. (Measure volume before heating.) Let precipitate form at room temperature for 60 minutes.

Weigh crucible containing Celite to nearest 0.1 mg, then wet and redistribute bed of Celite in crucible by using stream of 78% EtOH from wash bottle. Apply suction to draw Celite onto fritted glass as even mat. Maintain suction and quantitatively transfer precipitate from enzyme digest to crucible.

Wash residue successively with three 20 ml portions of 78% EtOH, two 10 ml portions of 95% EtOH, and two 10 ml portions of acetone. Gum may form with some samples, trapping liquid. If so, break surface film with spatula to improve filtration. Time for filtration and washing will vary from 0.1-6 hours, averaging 1.2 hour per sample. Long filtration times can be avoided by careful intermittent suction throughout filtration.

Dry crucible containing residue overnight in 70° C. vacuum oven or 105° C. air oven. Cool in desiccator and weigh to nearest 0.1 mg. Subtract crucible and Celite weight to determine weight of residue.

Analyze residue from sample of set of duplicates for protein and ash. Subtract protein and ash values from residue to obtain TDF.

Determination of blank:
blank = mg blank residue −

$$\frac{(\% \text{ protein in blank} + \% \text{ ash in blank}) \times \text{mg blank residue}}{100}$$

Determination of TDF (%):
TDF % = mg residue −

$$\frac{[(\% \text{ protein in residue} + \% \text{ ash in residue}) \times \text{mg residue}] - \text{blank}}{\text{mg sample (wt)}} \times 100$$

Total dietary fiber contents, DSC peak temperatures, solubility data, digestibility data and molecular weights for the samples are set out in Table 1. Example 1 containing no amylose exhibits a peak melting transition temperature at 78° C.; 2A comprising 100% amylose exhibits a peak melting transition temperature at 132° C. Examples 2B-2E show a peak transition temperature in the range of 119°-123° C., corresponding to the debranched amylose of sample 2A. Examples 3A and 3B, containing 70% amylose, were not debranched but were prepared by methods known in the art and exhibited peaks at about 150° C. The data show that the resistant starch products made by debranching exhibit a melting endotherm distinct from the peaks for starch products previously reported; from this it can be inferred that the instant resistant starch likely has a different structural composition from the resistant products previously disclosed.

TABLE 1

Characteristics of Resistant Starch Products

| Example | % amylose | treatment | recovery | TDF % by wt | Digestibility | DSC peak °C. | MW × 1000 | Solubility % in $H_2O$ |
|---|---|---|---|---|---|---|---|---|
| 1A | 0% amylose | debranched | spray-dried | 1.0 | 52.2 | 78 | 3-300 | 42.5 |
| 2A | 100% amylose | debranched | spray-dried | 50.3 | 18.7 | 132 | 143-146 | 0.0 |
| 2B | 70% amylose | debranched | spray-dried | 25.0 | 27.2 | 121 | 15-100 | 15 |
| 2C | 70% amylose | debranched | extruded | 30.0 | 22.6 | 124 | 17-70 | 9.1 |
| 2D | 70% amylose defatted | debranched | spray-dried | 32.4 | — | 119 | — | — |
| 2E | 70% amylose | debranched | salt ppt. 25% $MgSO_4$ | 40.9 | 22.7 | 122 | 17-50 | 7.0 |
| 3A | 70% amylose | hydrolyzed not debranched | ppt | N/A | 11.6 | 151 | 12-15 | 4.3 |
| 3B | 70% amylose | hydrolyzed not debranched | ppt/freeze-dried | N/A | 5.9 | 149 | 11-12 | ≦1.0 |
| 3C | 70% amylose | debranched | ppt/freeze- | 12.2 | 25.6 | 101 | 100-156 | 0.0 |

TABLE 1-continued

| | | | Characteristics of Resistant Starch Products | | | | |
|---|---|---|---|---|---|---|---|
| Example | % amylose | treatment | recovery dried | TDF % by wt | Digestibility | DSC peak °C. | MW × 1000 | Solubility % in H₂O |

Those skilled in the art will recognize, or be able to ascertain using no more than routine experimentation, many equivalents to the specific embodiments of the invention. Such equivalents are intended to be encompassed in the scope of the following claims.

We claim:

1. A starch product resistant to alpha-amylase digestion and derived from a starting starch containing at least 40% amylose, said starch product being essentially free of alpha-1,6-glucosidic bonds, characterized by a melting endotherm having a peak in the range of about 115°–135° C.

2. The resistant starch product according to claim 1 further characterized by a solubility in water at room temperature of greater than 7% weight/volume (gm/ml).

3. A starch product resistant to alpha-amylase digestion and derived from a starting starch containing at least 40% amylose, said starch product being essentially free of alpha-1,6-glucosidic bonds, characterized by a melting endotherm having a peak in the range of about 115°–135° C. made by the process consisting essentially of the steps of:
   (a) preparing an aqueous slurry of a starch that contains at least 40% amylose;
   (b) gelatinizing the starch slurry at temperatures of 120°–175° C. (250°–350° F.) and pressures of 1.05–10.5 kg/cm² (15–150 psi);
   (c) incubating the gelatinized starch with an effective amount of a debranching enzyme to hydrolyze essentially completely the 1,6-glucosidic bonds of the starch molecules;
   (d) isolating the debranched starch product by spray-drying.

4. The resistant starch product according to claim 3 further characterized by a solubility in water at room temperature of greater than 7% weight/volume (gm/ml).

5. The resistant starch product according to claim 3 in which the debranching enzyme is selected from the group consisting of pullulanase and isoamylase.

6. The resistant starch product according to claim 3 in which the resistant debranched starch product is isolated by extrusion.

7. A starch product resistant to alpha-amylase digestion and derived from a starting starch containing at least 40% amylose, said starch product being essentially free of alpha-1,6-glucosidic bonds, characterized by a melting endotherm having a peak in the range of about 115°–135° C. made by the process consisting essentially of the steps of:
   (a) preparing an aqueous slurry of a starch that contains at least 40% amylose;
   (b) gelatinizing the starch slurry at temperatures of 120°–175° C. (250°–350° F.) and pressure of 1.05–10.5 kg/cm² (15–150 psi);
   (c) incubating the gelatinized starch with an effective amount of a debranching enzyme to hydrolyze essentially completely the 1,6-glucosidic bonds of the starch molecules;
   (d) adding an inorganic salt to the debranched starch slurry in an amount effective to cause precipitation of the starch product;
   (e) incubating the starch and salt mixture at temperatures between 50°–100° C.;
   (f) initiating the precipitation of the resistant starch product by the addition of ethanol to the starch and salt mixture; and
   (g) isolating the resistant starch product.

8. The resistant starch product according to claim 7 in which the debranching enzyme is selected from the group consisting of pullulanase and isoamylase.

9. The resistant starch product according to claim 7 in which the inorganic salt is added to the starch in an amount of 10%–50% by weight of the starch solids.

10. The resistant starch product according to claim 7 in which the inorganic salts are selected from the group consisting of ammonium sulfate, sodium sulfate, magnesium sulfate, and sodium chloride.

11. The resistant starch product according to claim 7 in which the resistant starch product is isolated by extrusion.

* * * * *